(12) United States Patent
North et al.

(10) Patent No.: US 10,188,857 B2
(45) Date of Patent: Jan. 29, 2019

(54) LEAD IDENTIFICATION SYSTEM

(71) Applicant: Nuvectra Corporation, Plano, TX (US)

(72) Inventors: Richard North, Baltimore, MD (US); Scott F. Drees, Dallas, TX (US); John M. Swoyer, Andover, MN (US); Lawrence Kane, Roseville, MN (US); Jesse Geroy, Ham Lake, MN (US); Shahn S. Sage, Andover, MN (US); Elliot W. Bridgeman, Big Lake, MN (US); James Finley, Minneapolis, MN (US)

(73) Assignee: Nuvectra Corporation, Plano, TX (US)

( * ) Notice: Subject to any disclaimer, the term of this patent is extended or adjusted under 35 U.S.C. 154(b) by 221 days.

(21) Appl. No.: 15/183,878

(22) Filed: Jun. 16, 2016

(65) Prior Publication Data

US 2016/0287864 A1    Oct. 6, 2016

Related U.S. Application Data

(63) Continuation of application No. 13/898,845, filed on May 21, 2013, now Pat. No. 9,517,333, which is a (Continued)

(51) Int. Cl.
*A61N 1/00* (2006.01)
*A61N 1/05* (2006.01)
(Continued)

(52) U.S. Cl.
CPC ............ *A61N 1/0558* (2013.01); *A61B 90/90* (2016.02); *A61B 90/92* (2016.02); *A61B 90/94* (2016.02);
(Continued)

(58) Field of Classification Search
USPC .................................................. 607/116–117
See application file for complete search history.

(56) References Cited

U.S. PATENT DOCUMENTS 8,473,074 B2    6/2013   North et al.
8,744,595 B2    6/2014   Tronnes
(Continued)

FOREIGN PATENT DOCUMENTS

EP    1929972    11/2008

OTHER PUBLICATIONS

European Search Report, Application EP12180125, dated Nov. 22, 2012.

*Primary Examiner* — Nicole F Johnson
(74) *Attorney, Agent, or Firm* — Haynes and Boone, LLP; Eric Q. Li

(57) ABSTRACT

In some examples, a lead identification system includes a first set of first lead indicators and a second set of second lead indicators. Each of the first lead indicators is configured to removably attach to at least one of a first therapy delivery element, a first epidural needle, or a first connector to uniquely identify at least one of the first therapy delivery element, the first epidural needle, or the first connector during implantation of the first therapy delivery element in the patient. Each of the second lead indicators is configured to removably attach to at least one of a second therapy delivery element, a second epidural needle, or a second connector to uniquely identify at least one of the second therapy delivery element, the second epidural needle, or the second connector during implantation of the second therapy delivery element in the patient.

20 Claims, 14 Drawing Sheets

Related U.S. Application Data continuation of application No. 13/222,330, filed on Aug. 31, 2011, now Pat. No. 8,473,074.

(51) Int. Cl.
| | | |
|---|---|---|
| *A61B 90/90* | (2016.01) |
| *A61B 90/92* | (2016.01) |
| *A61B 90/94* | (2016.01) |
| *A61N 1/372* | (2006.01) |
| *A61B 90/00* | (2016.01) |

(52) U.S. Cl.
CPC .. *A61N 1/37241* (2013.01); *A61B 2090/3937* (2016.02); *A61B 2090/3962* (2016.02)

(56) References Cited

U.S. PATENT DOCUMENTS

| | | |
|---|---|---|
| 2004/0260310 A1* | 12/2004 | Harris ................ A61N 1/0553 606/117 |
| 2006/0229529 A1 | 10/2006 | Wright |
| 2009/0216306 A1 | 8/2009 | Barker |
| 2009/0248124 A1 | 10/2009 | Pianca et al. |
| 2010/0137943 A1 | 6/2010 | Zhu |
| 2011/0112609 A1 | 5/2011 | Peterson |

* cited by examiner

LEAD IDENTIFICATION SYSTEM

CLAIM OF PRIORITY

This application is a continuation of U.S. patent application Ser. No. 13/898,845 filed May 21, 2013, now U.S. Pat. No. 9,517,333, which is a continuation of U.S. patent application Ser. No. 13/222,330, filed on Aug. 31, 2011, now U.S. Pat. No. 8,473,074, which are incorporated by reference herein in their entirety.

FIELD

The present disclosure relates to a lead identification system for multiple neurostimulation leads during implantation within a living body.

BACKGROUND

Implantable neurostimulation systems have proven therapeutic in a wide variety of diseases and disorders. These implantable neurostimulation systems typically include one or more stimulation leads implanted at the desired stimulation site and an implantable neurostimulator, such as an implantable pulse generator (IPG), implanted remotely from the stimulation site, but coupled either directly to the stimulation leads or indirectly to the stimulation leads via one or more lead extensions in cases where the length of the stimulation leads is insufficient to reach the IPG.

In the context of an SCS procedure, one or more stimulation leads are introduced through the patient's back into the epidural space under fluoroscopy, such that the electrodes carried by the leads are arranged in a desired pattern and spacing to create an electrode array. After proper placement of the stimulation leads at the target area of the spinal cord, the leads are anchored in place at an exit site to prevent movement of the stimulation leads. Whether lead extensions are used or not, the proximal ends of the stimulation leads exiting the spinal column are passed through a tunnel subcutaneously formed along the torso of the patient to a subcutaneous pocket (typically made in the patient's abdominal or buttock area) where a neurostimulator is implanted.

The stimulation leads are then connected directly to the neurostimulator by inserting the proximal ends of the stimulation leads within one or more connector ports of the IPG or connected to lead extensions, which are then inserted into the connector ports of the IPG. The IPG can then be operated to generate electrical pulses that are delivered, through the electrodes, to the targeted tissue, and in particular, the dorsal column and dorsal root fibers within the spinal cord.

Oftentimes, multiple lead bodies may extend from the spinal region of the patient. For example, multiple percutaneous leads may be implanted within the patient adjacent the spinal cord, or in the case of paddle leads, multiple lead tails may extend from the paddle, with each lead tail being coupled to specific electrodes on the paddle. Because the programming of the IPG will depend upon the physical locations of the electrodes relative to the patient's spinal cord, the proximal ends of the lead bodies are labeled before passing them through the tunneling straw, so that the surgeon can keep track of which set of electrodes is connected to which connector port on the implanted IPG (which may include up to four ports in the near future), or if multiple IPGs are to be implanted, which set of electrodes is connected to which IPG.

One technique used by surgeons to identify the lead bodies is to tie sutures around the proximal ends of the lead bodies prior to introducing them through the tunneling straw; for example, one suture around a first lead body, two sutures around a second lead body, three sutures around a third lead body, etc. Once the proximal ends of the lead bodies exit the tunneling straw, the surgeon can then identify each lead body (and thus the corresponding electrodes) by the number of sutures tied to the respective lead body, thereby allowing the lead body to be connected to the correct port on the IPG.

While this technique can be successfully employed to identify lead bodies, it considerably extends the length of the surgery time, which is undesirable. In some cases, the identification features, such as different colors or markings, can be incorporated into the proximal ends of the lead bodies, such that the lead bodies can be identified as they exit the tunneling straw. If the lead bodies are inserted into the incorrect connector ports, intra-operative testing of the lead placement may be compromised. Additional surgical time may be wasted to identify and correct the connection problem. If the errors remain unidentified, the patient may leave the operating room with the lead bodies incorrectly connected. During post-operative fitting, additional time may then be lost identifying and compensating for lead bodies that are not in the proper connector ports. This ultimately can result in sub-optimal therapy.

BRIEF SUMMARY

The present disclosure relates to a lead identification system for multiple neurostimulation leads that permits the surgeon to track electrodes on a particular lead to the correct connectors on the implantable pulse generator.

The present lead identification system provides corresponding lead indicators that permit the surgeon to track the electrodes of a particular therapy delivery element to the correct connectors on an implantable pulse generator. The lead indicators are preferably releasably attachable to the components of the neurostimulation system and can be shifted or reconfigured by the surgeon during the procedure. Consequently, the components of the neurostimulation system, such as the epidural needles, the leads and lead extensions, lead clips, lead anchors, stylets, internal and external pulse generators, and trial cables can all be generic without any labels or indicia. The use of removable lead indicators dramatically reduces the inventory of components for the neurostimulation system.

One embodiment is directed to a method of implanting a plurality of trial neurostimulation leads in a patient. An epidural needle is inserted into the patient for each trial lead. A trial lead is inserted through each epidural needle and positioned in the patient. A removable lead indicator is attached to each epidural needle. Proximal portions of the trial leads are attached to a clip with corresponding lead indicators. The proximal ends of the trial leads are electrically coupled to connectors having corresponding lead indicators on the trial cable. Trial stimulation of the trial leads is conducted to confirm lead placement. Corresponding lead indicator stylets are inserted in lumens of each of trial lead. The trial leads are disconnected from the trial cable. The epidural needles are removed from the patient by sliding the epidural needles off the trial leads. The incisions around the trial leads are closed. The trial leads are electrically coupled to connectors having corresponding lead indicators on an external pulse generator. The neurostimulation leads are operated during a trial period.

The removable lead indicators can be one or more of color indicators, tactile indicators, alpha-numeric indicators, or a combination thereof.

The present disclosure is also directed to a method of implanting a plurality of permanent neurostimulation leads in a patient. An epidural needle is inserted into the patient for each permanent lead. A permanent lead is inserted through each epidural needle and positioned in the patient. A removable lead indicator is attached to each epidural needle. Proximal portions of the permanent leads are attached to a clip with corresponding lead indicators. The proximal ends of the permanent leads are electrically coupled to connectors having corresponding lead indicators on the trial cable. Trial stimulation of the permanent leads is conducted to confirm lead placement. Corresponding lead indicator stylets are inserted in lumens of each of permanent lead. The permanent leads are disconnected from the trial cable. The epidural needles are removed from the patient by sliding the epidural needles off the permanent leads. The permanent leads are attached to the patient using anchors having corresponding lead indicators. Proximal ends of the permanent leads with the corresponding lead indicator stylets are passed through one or more lumens to an implantable pulse generator located at a remote implantation site in the patient. The corresponding lead indicator stylets are removed from the lumens of the permanent leads. The proximal ends of the permanent leads are electrically coupled to connectors having corresponding lead indicators on an implantable pulse generator. The incision sites around the permanent leads and the implantable pulse generator are closed.

The present disclosure is also directed to a method of implanting a plurality of permanent neurostimulation leads with trial lead extensions in a patient. An epidural needle is inserted into the patient for each permanent lead. A permanent lead is inserted through each epidural needle and positioned in the patient. A removable lead indicator is attached to each epidural needle. Proximal portions of the permanent leads are attached to a clip with corresponding lead indicators. The proximal ends of the permanent leads are electrically coupled to connectors having corresponding lead indicators on a trial cable. A trial stimulation of the permanent leads is conducted to confirm lead placement. Corresponding lead indicator stylets are inserted in lumens of each of the permanent leads. The permanent leads are disconnected from the trial cable. The epidural needles are removed from the patient by sliding the epidural needles off the permanent leads. The permanent leads are attached to the patient using anchors having corresponding lead indicators. The removable lead indicator stylets are transferred from the permanent leads to lumens at proximal ends of the trial lead extensions. Distal ends of the trial lead extensions are attached to proximal ends of the corresponding permanent leads. Proximal ends of the trial lead extensions with the corresponding lead indicator stylets are passed through one or more lumens to a remote implantation site in the patient. The corresponding lead indicator stylets are removed from the lumens of the trial lead extensions. The trial leads are electrically coupled to connectors having corresponding lead indicators on an external pulse generator. Trial neurostimulation is conducted using the external pulse generator.

The present disclosure is also directed to a method of implanting a plurality of permanent neurostimulation leads without lead extensions in a patient. The incision site where trial lead extensions are connected to the permanent leads is opened. The permanent leads are disconnected from the trial lead extensions. Removable lead indicator stylets are inserted in lumens at proximal ends of the permanent leads. The trial lead extensions are removed from the patient. Proximal ends of the permanent leads with the corresponding lead indicator stylets are passed through one or more lumens to a remote implantation site in the patient. The corresponding lead indicator stylets are removed from the lumens of the permanent leads. The permanent leads are electrically coupled to connectors on an implantable pulse generator having corresponding lead indicators. The implantable pulse generator is sealed in the implantation site in the patient.

The present disclosure is also directed to a method of implanting a plurality of permanent neurostimulation leads with permanent lead extensions in a patient. The incision site where trial lead extensions are connected to the permanent leads is opened. The permanent leads are disconnected from the trial lead extensions. Removable lead indicator stylets are inserted in lumens at proximal ends of the permanent leads. The trial lead extensions are removed from the patient. The removable lead indicator stylets are transferred to lumens at proximal ends of the permanent lead extensions. Permanent lead extensions are attached to the permanent leads. The proximal ends of the permanent lead extensions with the corresponding lead indicator stylets are passed through one or more lumens to a remote implantation site in the patient. The corresponding lead indicator stylets are removed from the lumens of the permanent lead extensions. The permanent lead extensions are electrically coupled to connectors having corresponding lead indicators on an implantable pulse generator. The implantable pulse generator is sealed in the implantation site in the patient.

The present disclosure is also directed to a lead identification system for tracking a plurality of neurostimulation leads during implantation in a patient. The lead identification system includes a plurality of removable lead indicators each adapted to attach to one of a plurality of epidural needles to identify the leads. One embodiment includes rotating lead indicators attach to each of the epidural needles wherein a rotational orientation of the rotating lead indicators uniquely identify each of the therapy delivery elements. At least one clip adapted to releasably attach to proximal ends of the leads is provided with corresponding lead indicators. The trial cable for conducting trial stimulation includes connectors with corresponding lead indicators. A plurality of removable lead indicator stylets are provided for insertion into lumens at the proximal ends of the leads. A pulse generator is provided with connectors having corresponding lead indicators. The various removable lead indicators permit a surgeon to track electrodes on a particular lead to the corresponding connectors on the pulse generator.

The removable lead indicators can be one or more of color indicators, tactile indicators, alpha-numeric indicators, or a combination thereof. The leads can be trial leads or permanent leads. The pulse generator can be an external pulse generator for conducting trials or an implantable pulse generator. The lead identification system optionally includes one or more lead anchors adapted to attach the leads to the patient with corresponding lead indicators.

DETAILED DESCRIPTION OF SOME EMBODIMENTS

The description that follows relates to a spinal cord stimulation (SCS) system. However, it is to be understood that while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
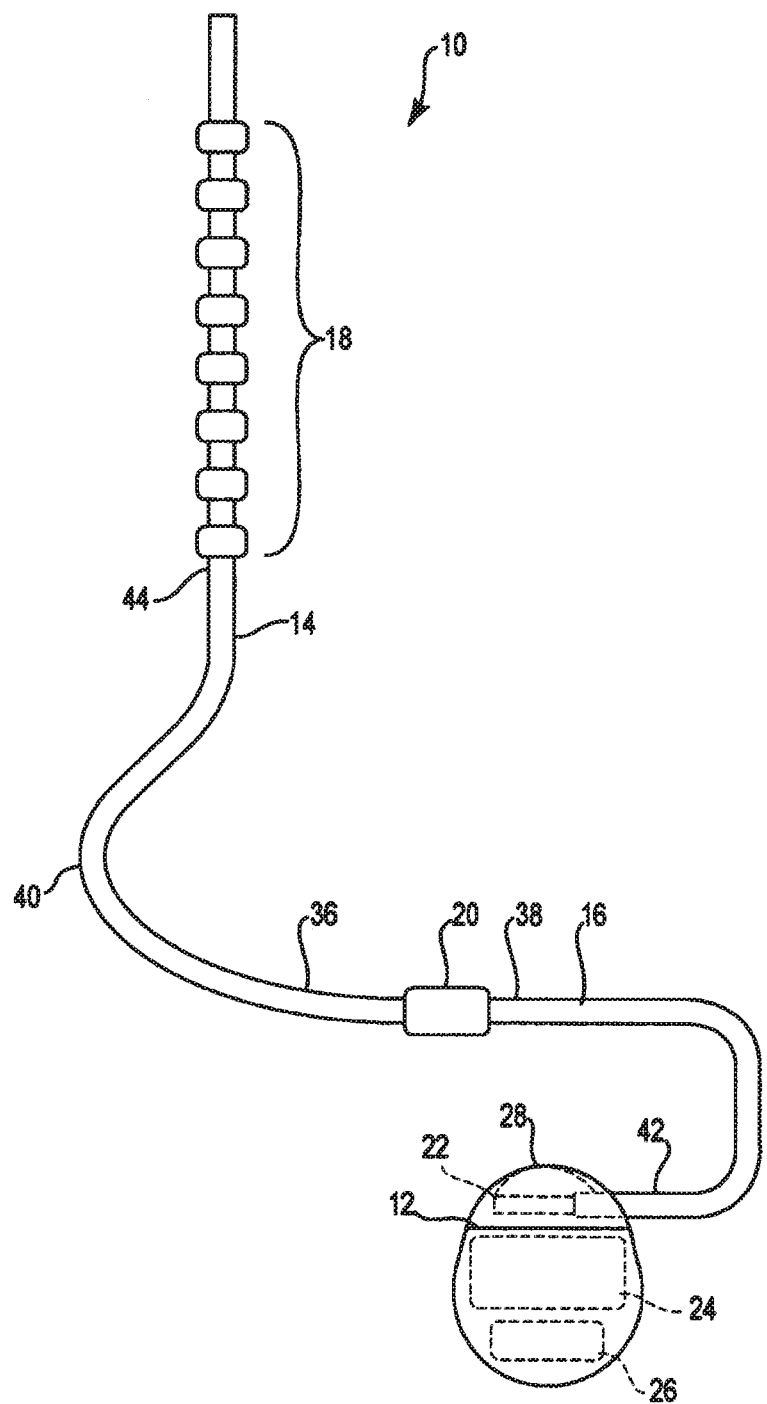
FIG. 1 is a schematic illustration of a therapy delivery system.

FIGS. 1 illustrates a generalized therapy delivery system 10 that may be used in spinal cord stimulation (SCS), as well as other stimulation applications. The therapy delivery system 10 generally includes an implantable pulse generator 12 ("IPG") ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be co-extruded with the conductors.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22. In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
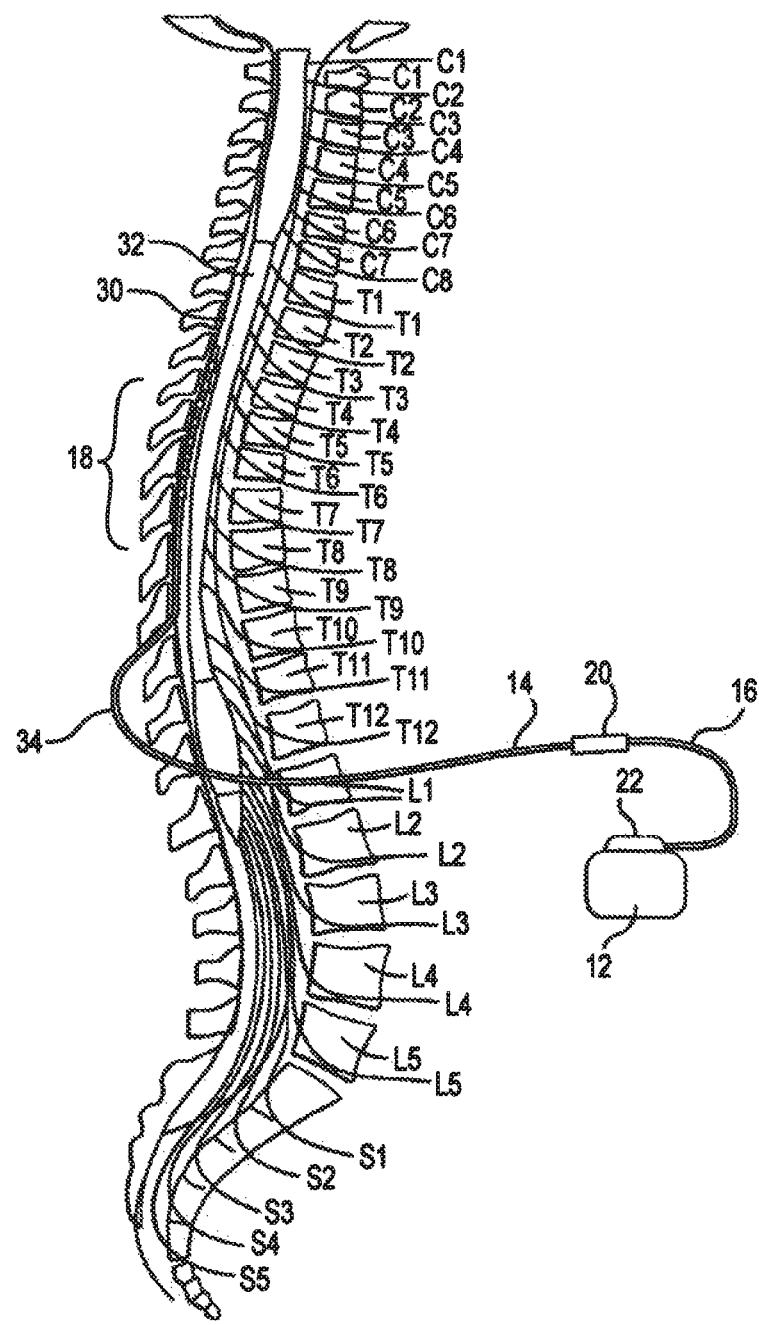
FIG. 2 is a schematic illustration of an environment for a therapy delivery system in accordance with an embodiment of the present disclosure.

FIG. 2 illustrates the therapy delivery element 14 implanted in the epidural space 30 of a patient in dose proximity to the dura, the outer layer that surrounds the spinal cord 32, to deliver the intended therapeutic effects of a spinal cord electrical stimulation. The target stimulation sites may be anywhere along the spinal cord 32, such as for example proximate the sacral nerves.

Figure 3:
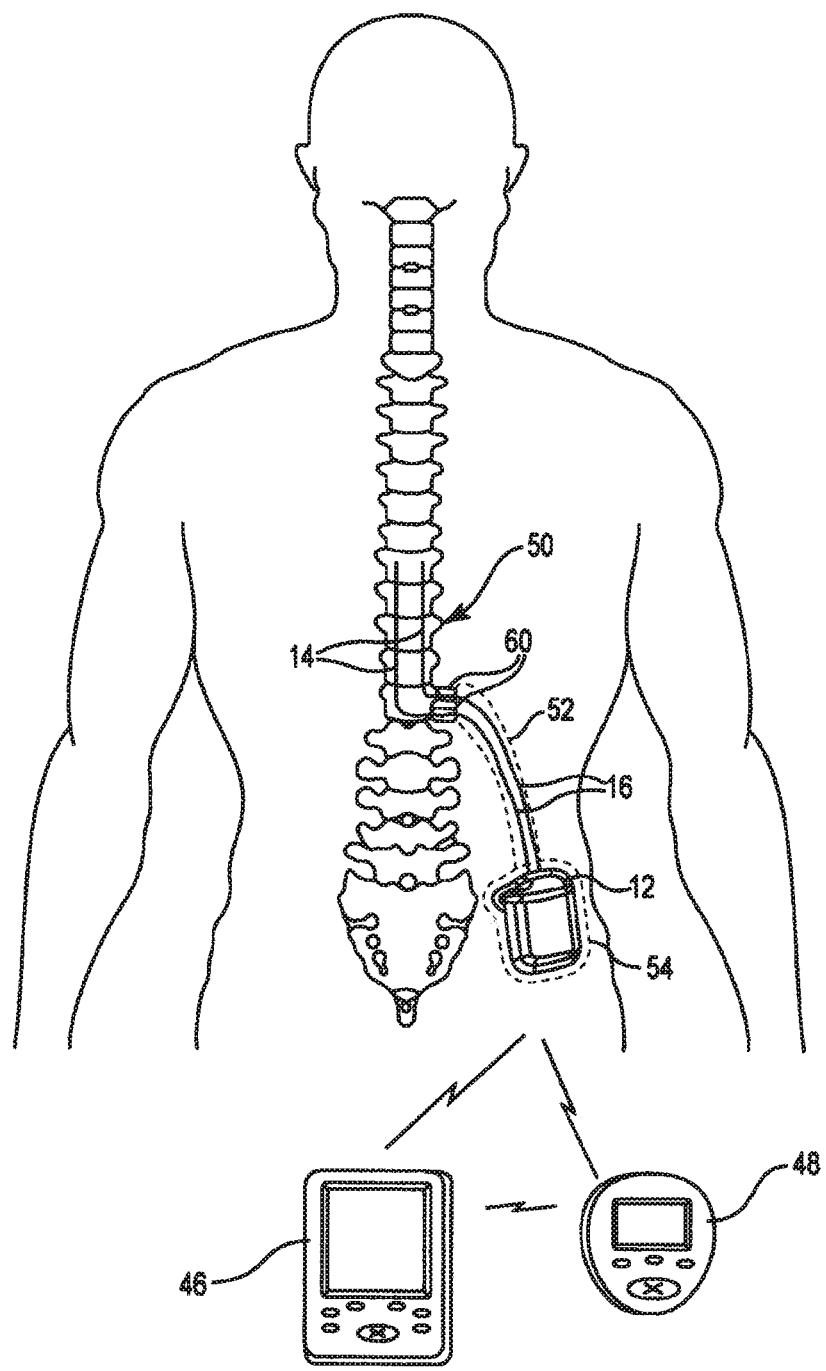
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 3 also illustrates a general environment that may benefit from use of a tunneling tool in accordance with an embodiment of the present disclosure. Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" are used interchangeably, unless content clearly dictates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 4:
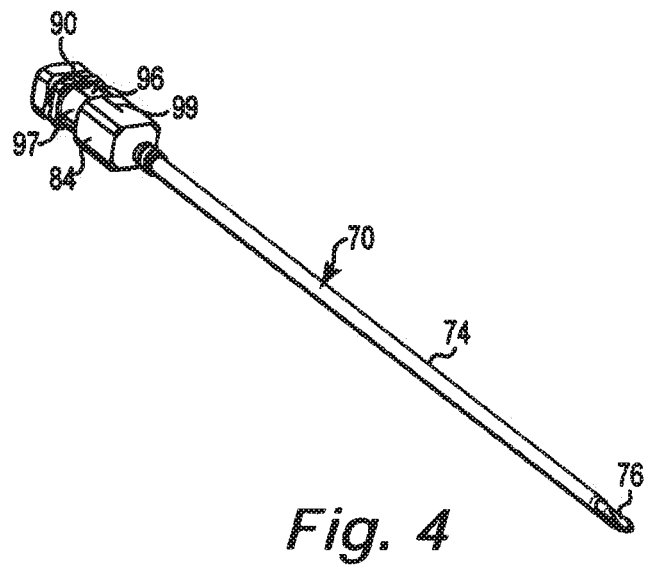
FIG. 4 is a perspective view of epidural needle adapted to receive a removable lead indicator in accordance with an embodiment of the present disclosure.

FIG. 4 illustrates an epidural needle 70 configured to permit therapy delivery element 78 to be advanced into, and withdrawn from, an epidural space 72 (see FIG. 5) in accordance with an embodiment of the present disclosure. The epidural needle 70 includes an outer cannula 74 and an inner cannula 76. Removal of the inner cannula 76 creates and opening sized to receive a therapy delivery element 78. An epidural needle suitable for implanting the therapy delivery element 78 is disclosed in commonly-assigned U.S. patent application Ser. No. 13/046,282, entitled Epidural Needle for Spinal Cord Stimulation, filed Mar. 11, 2011, which is hereby incorporated by reference.

Figure 5:
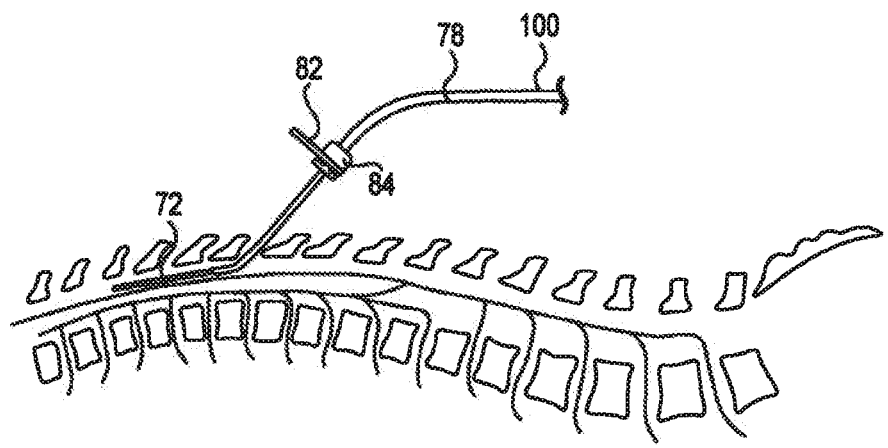
FIG. 5 is a schematic illustration of a removable lead indicator on an epidural needle during implantation of a therapy delivery element in accordance with an embodiment of the present disclosure.

FIG. 5 is a schematic illustration of the epidural needle 70 located in the epidural space 72 between the L1 and T12 vertebrae. The therapy delivery element 78 is inserted through the epidural needle 70 and positioned in the epidural space 72 of the patient. Lead indicator 82 is attached to hub 84 of the epidural needle 70. The lead indicator 82 can also be attached to the needle portion 70.

In one embodiment, the lead indicators 82 for the present lead identification system are color coded. Any color scheme can be used. One approach is the red-yellow-green color scheme used for traffic lights throughout the world, where the red light is always on the top and the green on the bottom. A similar color scheme can be used on the trial cable and the connector block on the IPG 12 so the colors also have a fixed spatial relationship.

In another embodiment, the indicators 82 include both a color scheme and tactile indicators so the surgeon can identify the indicators both visually and by feel. For example, the lead indicators can have different textures (e.g., smooth-textured-rough surface finish) or a unique shape (e.g., circle-square-triangle) that correspond to the red-yellow-green color scheme. In yet another embodiment, the indicators include alpha-numeric characters. While the present lead indicators are preferably color coded, reference to a lead indicator should be understood to include a variety of indicators for use in the present lead identification system.

Figure 6:
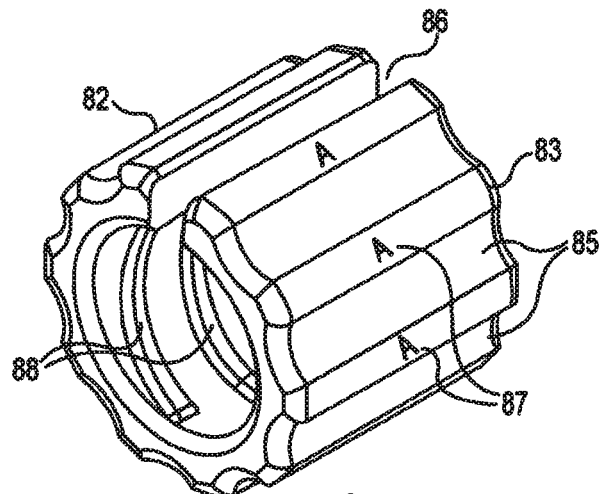
FIG. 6 is a perspective view of a removable lead indicator suitable for attachment to an epidural needles in accordance with an embodiment of the present disclosure.
Figure 7:
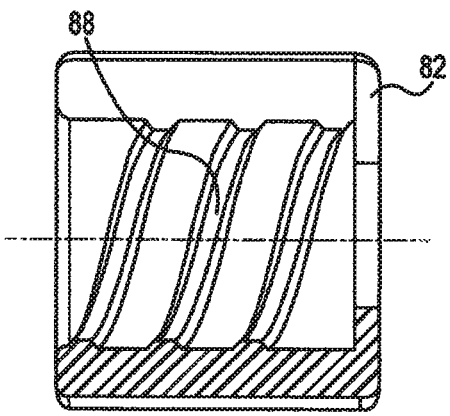
FIG. 7 is a side sectional view of the lead indicator of FIG. 6.

FIGS. 6 and 7 illustrate an embodiment of a removable lead indicator 82 suitable for attachment to the hub 84 of the epidural needles 70 in accordance with an embodiment of the present disclosure. The removable lead indicator 82 includes slot 86 that permits it to engage with outer cannula 74 illustrated in FIG. 4. In one embodiment, the lead indicator 82 includes internal threads 88 that are configured to engage external threads 90 on the hubs 84. Alternatively, the lead indicator 82 can be snap-fit onto narrow portion 96 of the hubs 84.

In one embodiment, the lead indicators 82 are different colors (e.g., red-yellow- green). In another embodiment, outer surface 83 includes different sized recesses 85 corresponding to the red-yellow-green lead indicators 82. In yet another embodiment, alpha-numeric indicators 87 can be added to the lead indicator 82. The different colors, alpha-numeric indicators, and recesses 85 can be used separately or in combination in accordance with the present lead identification system.

In another embodiment best illustrated in FIG. 4, an elastomeric sleeve 97 is positioned in the narrow portion 96. 111e sleeve 97 includes indicia, such as for example different color strips. By rotating the sleeve 97 the surgeon can align the indicia marker 99 on the hub 84. Epidural needles 70 with rotating sleeves 97 can be configured to identify any of the therapy delivery elements 78.

Figure 8:
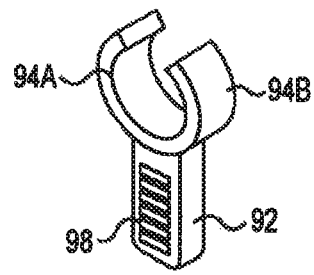
FIG. 8 is a perspective view of an alternate removable lead indicator in accordance with an embodiment of the present disclosure.

FIG. 8 illustrates an alternate removable lead indicator 92 suitable for attachment to the epidural needle 70 of FIG. 4. Flexible arms 94A, 94B elastically deform to permit engagement with the outer cannula 74 and/or the hub 84. The lead indicators can include a variety of indicia, such as color-coding. In the illustrated embodiment, the lead indicator 92 also includes an identifying texture 98. For example, the lead indicators 92 can include smooth-textured-rough surfaces 98 used as part of the present lead identification system.

Figure 9:
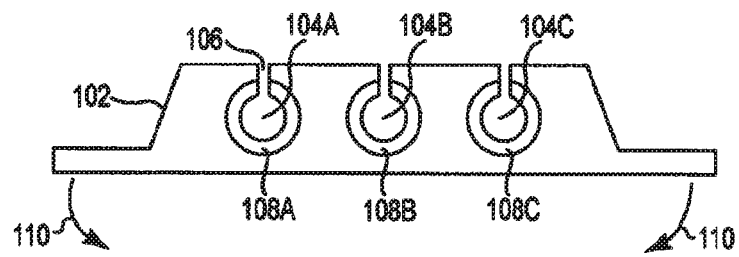
FIG. 9 is a side view of a clip having lead indicators adapted to attach to therapy delivery elements in accordance with an embodiment of the present disclosure.

FIG. 9 illustrates a clip 102 adapted to attach proximal ends 100 of the therapy delivery elements 78 to the patient in accordance with an embodiment of the present disclosure. The proximal ends 100 of the therapy delivery elements 78 are preferably clipped or otherwise attached to the patient or surgical drape during various phases of the implantation process. In the illustrate embodiment, the clip 102 includes three discrete receiving openings 104A, 104B, 104C ("104") sized to receive proximal ends 100 of three therapy delivery elements 78. Each receiving opening 104 includes a slot 106 to permit insertion of the therapy delivery element 78 and a lead indicator 108A, 108B, 108C ("108"), such as for example color-coded inserts. In one embodiment, the clip 102 is constructed from an elastomeric material. By bending the clip 102 in the direction 110, the size of the slots 106 increases to facilitate engagement of the therapy delivery elements 78. The clip 102 can be attached using clamps, adhesive tape, or a variety of other techniques.

Figure 10:
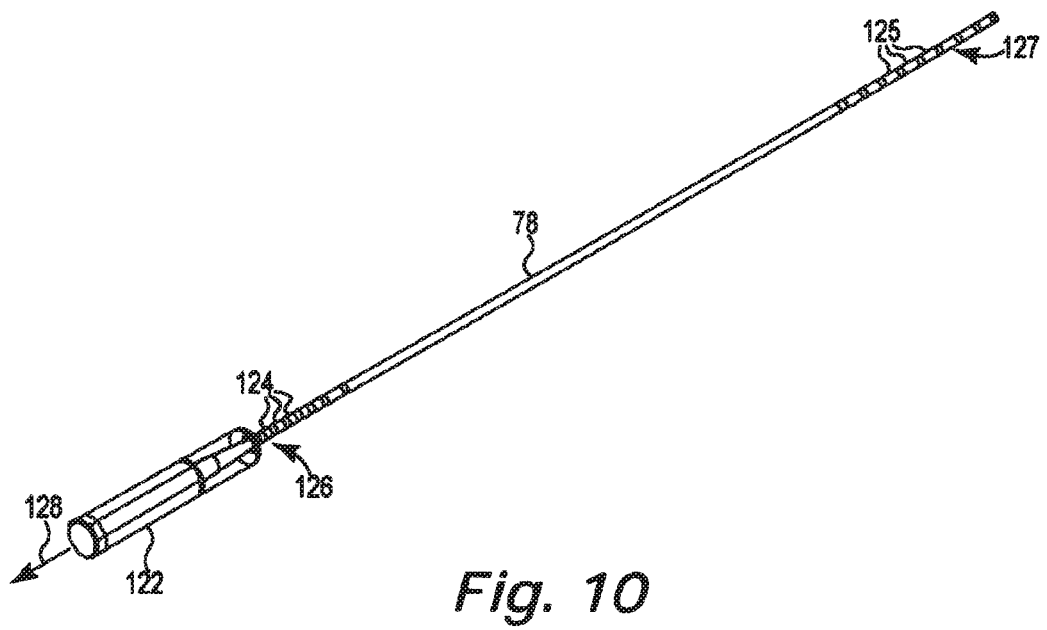
FIG. 10 is a perspective view of a stylet-lead assembly in accordance with an embodiment of the present disclosure.

FIG. 10 illustrates one possible embodiment of the therapy delivery element 78 for use with the present lead identification system. Stylet handle 122 is attached to a stylet wire that extends through lumen 142 (see FIG. 12) of the therapy delivery element 78. In the illustrated embodiment, the style handle 122 covers one or more of the contacts 124 at proximal end 126 of the therapy delivery element 78. The stylet handle 122 is preferably detached from the therapy delivery element 78 and moved in direction 128 a sufficient amount to expose all of the contacts 124. Each contact 124 has a corresponding electrode 125 at the distal end 127 of the therapy delivery element 78.

Figure 11:
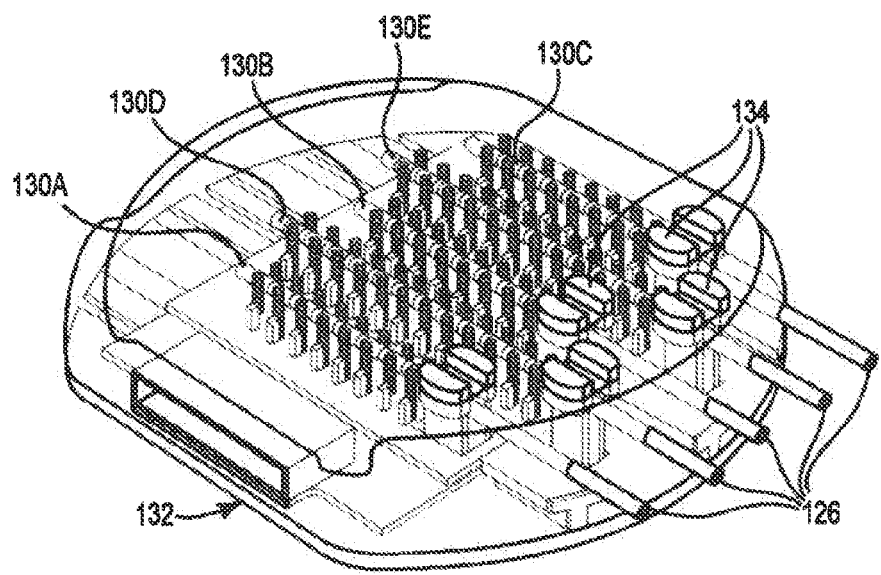
FIG. 11 is a perspective view of a trial cable connector with lead indicators in accordance with an embodiment of the present disclosure.

As illustrated in FIG. 11, the exposed contacts 124 on the proximal ends 126 are then attached to connector blocks 130A, 130B, 130C, 130D, 130E ("130") on trial cable connector 132. In the illustrated embodiment, trial cable connector 132 includes three eight contact connector blocks 130A, 130B, 130C and two twelve contact connector blocks 130D, 130E. Trial stimulation of the therapy delivery elements 78 is then conducted as is known by those of skill in the art. The connector blocks 130 include lead indicators 134, such as for example, color coding, alpha-numeric symbols, geometric shapes, and a variety of other lead indicators to identify the particular connector blocks 130.

Figure 12:
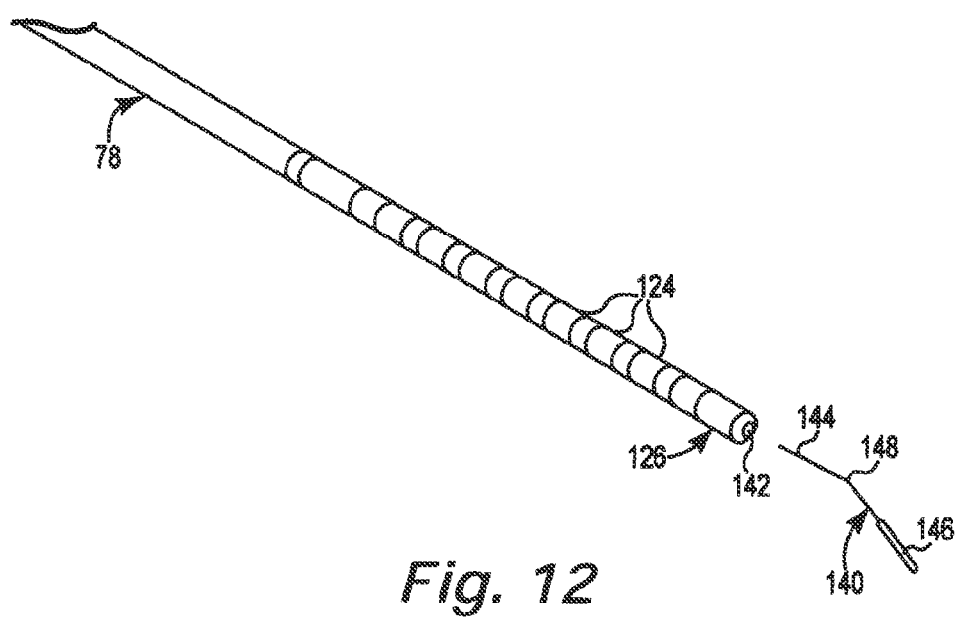
FIG. 12 is a perspective view of a removable lead indicator adapted for insertion into a lumen of a therapy delivery element in accordance with an embodiment of the present disclosure.

Once the surgeon has confirmed that the therapy delivery elements 78 are located in the desired location within the epidural space 72, the stylet handle 122 and the attached stylet are removed. As illustrated in FIG. 12, removable lead indicators 140 are inserted in the lumen 142 at proximal end 126 of each therapy delivery element 78. In the illustrated embodiment, the removable lead indicators 140 each include a stylet wire 144 and a color indicator 146. The color indicators 146 preferably have a diameter less than or equal to the diameter of the therapy delivery element 78. In one embodiment, color indicators 146 are colored silicone tubing that compressively engages with the stylet wire 144. A clear shrink wrap is optionally applied over the silicone tubing.

The stylet wires 144 optionally include bends 148 to increase friction with the lumen 142. The bends 148 reduce the chance of the removable lead indicator 140 from inadvertently falling out of the lumens 142.

After a removable lead indicator 140 is inserted in each lumen 142, the therapy delivery elements 78 are disconnected from the trial cable connector 132. At this point, the proximal ends 126 of the therapy delivery elements 78 are free and the epidural needles 70 can be removed from the patient and slid off the proximal ends 126. The therapy delivery elements 78 will typically need to be temporarily disconnected from the clip 102 to remove the epidural needles 70.

The present lead identification system provides corresponding lead indicators 82, 92, 102, 134, 140, and 150 that permit the surgeon to track the electrodes 125 of a particular therapy delivery element 78 to the correct connectors 124 on the implantable pulse generator 12. Since the lead indicators 82, 92, 102, 134, 140, and 150 are releasably attachable to the components of the neurostimulation system, they can be shifted or reconfigured by the surgeon during the procedure. For example, two therapy delivery elements switch position during placement, or test stimulation shows the midline to be offset from its anticipated location. The lead indicators are easily reconfigured during the procedure to reflect the actual lead placement. As a result, the components of the neurostimulation system, such as the epidural needles, the leads and lead extensions, lead clips, lead anchors, stylets, internal and external pulse generators, and trial cables can be generic without any labels or indicia. The use of removable lead indicators dramatically reduces the inventory of components for the neurostimulation system. As used herein, "corresponding lead indicator" refers to a lead indicator with indicia that can be correlated with indicia on at least one other lead indicator.

Figure 13:
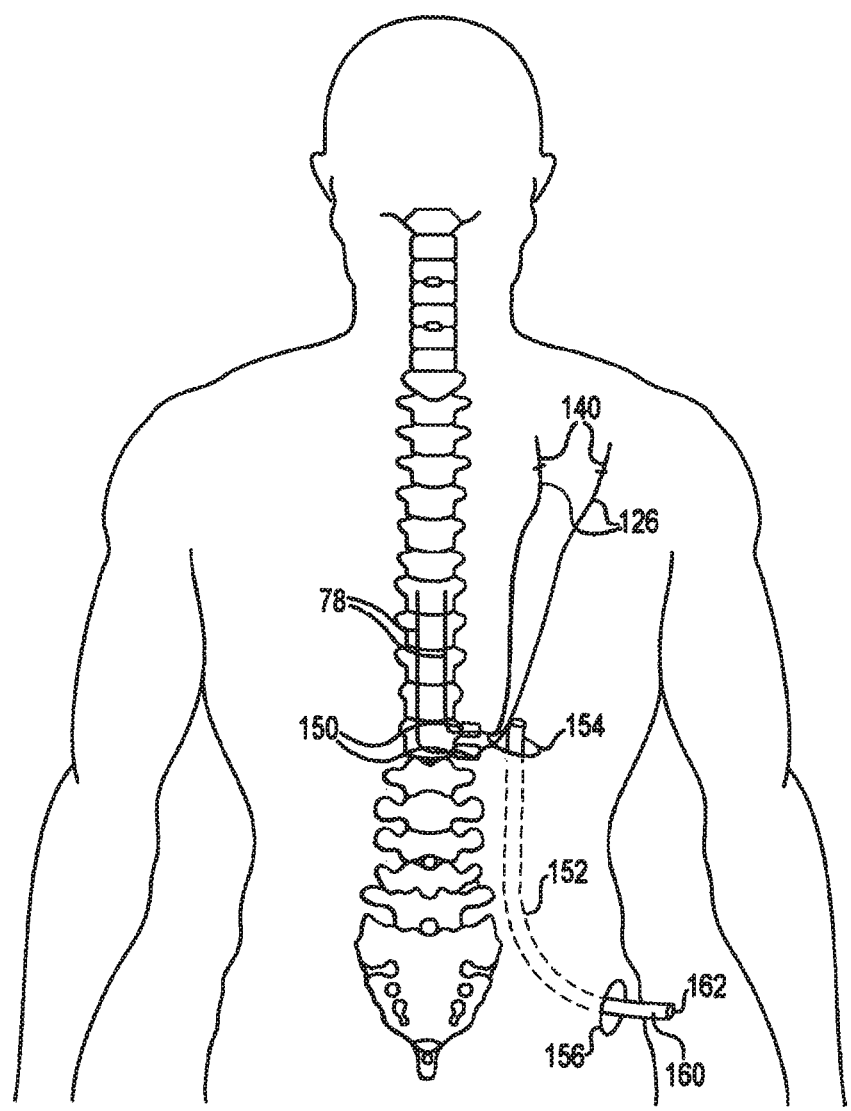
FIG. 13 illustrates a method of using a lead identification system in accordance with an embodiment of the present disclosure.

As illustrated in FIG. 13, each therapy delivery element 78 are attached to the patient with an anchor 150 that preferably includes a lead indicator in accordance with an embodiment of the present disclosure. In one embodiment, the anchors 150 are color coded to identify the individual therapy delivery elements 78. Suitable anchors 150 are disclosed in commonly-assigned U.S. patent application Ser. Nos. 13/045,874, entitled Anchor for Implantable Medical Device, filed Mar. 11, 2011; Ser. No. 13/045,947, entitled Anchor Sleeve for Implantable Sleeve, filed Mar. 11, 2011; and Ser. No. 13/046,182, entitled Pre-Sutured Anchor for Implantable Leads, filed Mar. 11, 2011, all of which are hereby incorporated by reference.

The surgeon then creates a pathway 152 between the incision site 154 near the anchors 150 and the incision site 156 for the subcutaneous pocket 54 holding the implantable pulse generator 12 (see FIG. 3). The pathway 152 is preferably created using a tunneling tool, such as disclosed in commonly-assigned U.S. patent application Ser. No. 13/046,144, entitled Tunneling Tool for Implantable Leads, filed Mar. 11, 2011, which is hereby incorporated by reference.

After the tunneling step is completed, sheath 160 extends along the pathway 152. Proximal ends 126 of the therapy delivery elements 78 are passed through lumen 162 in the sheath 160 to the incision site 156. The sheath 160 is then removed from the patient by pulling it through the incision site 156 so that the therapy delivery elements 78 extend through the pathway 152 and out the incision site 156. The lead indicators 140 are then removed from the lumens 142 at the proximal ends 126 of the therapy delivery elements 78. Each therapy delivery element 78 is attached to a corresponding connector 22 on the implantable pulse generator 12. The connectors 22 are preferably color coded. The implantable pulse generator 12 is implanted in the subcutaneous pocket 54 and the incision sites 154, 156 closed.

As will be discussed in detail below, the present method can be used for implanting trial leads or permanent leads, using a variety of procedures. While the following flow charts use color coded lead indicators, it will be appreciated that a wide variety of other indicators can be used with the methods of the present lead identification system.

Figure 14:
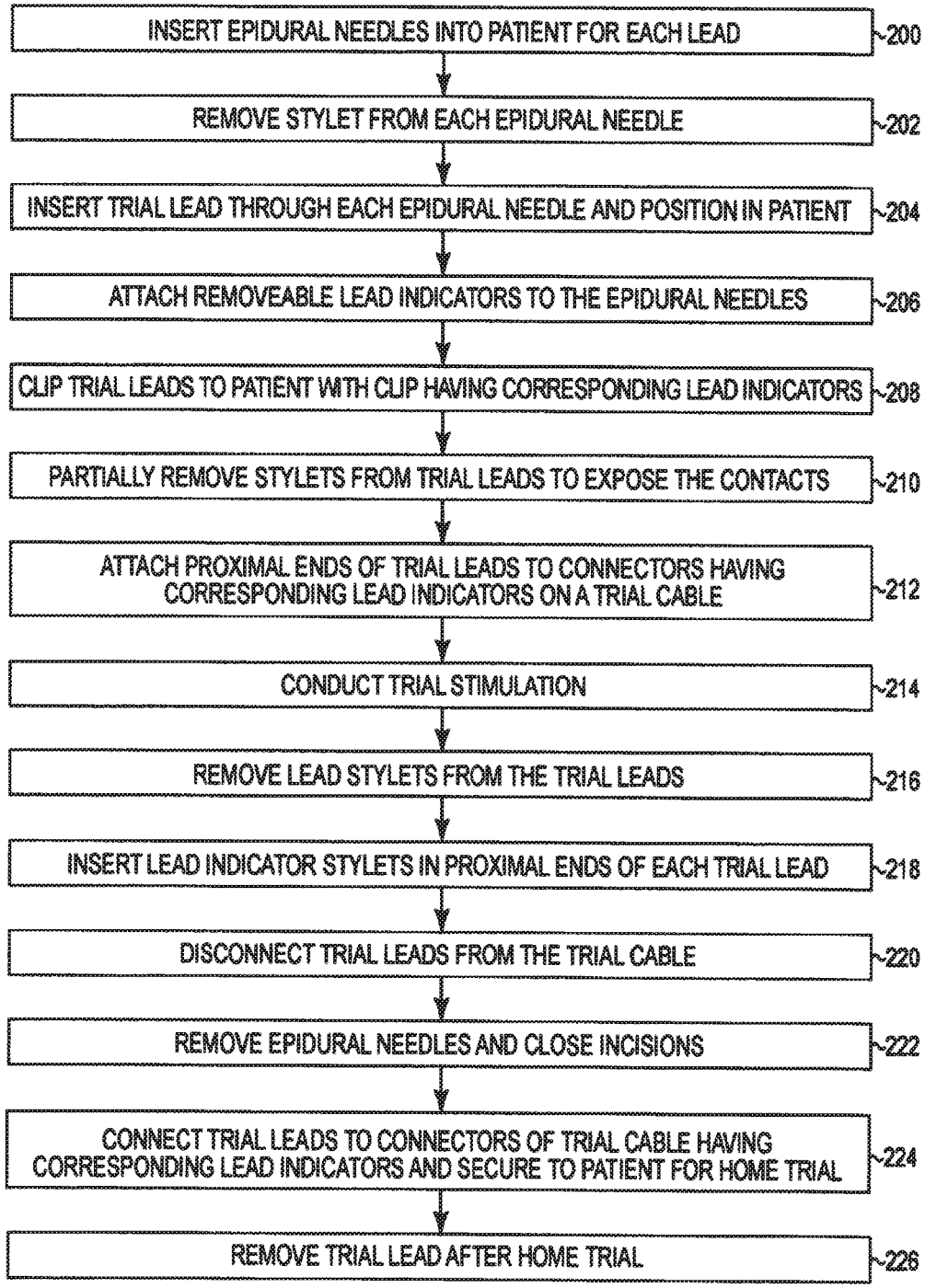
FIG. 14 is a flow chart summarizing a method for implanting a plurality of trial leads using a lead identification system in accordance with an embodiment of the present disclosure.

FIG. 14 is a flow chart summarizing a method for implanting a plurality of trial leads using a lead identification system in accordance with an embodiment of the present disclosure. An epidural needle is inserted into the patient for each trial lead (200). The stylets are removed from the epidural needles (202). The trial leads are inserted through each epidural needle and positioned in the patient (204). A lead indicator is attached to each epidural needle (206). Proximal portions of the trial leads are preferably clipped to the patient using a clip with a lead indicator (208). The stylets are partially removed from each of the trial leads to expose the contacts (210). The contacts at the proximal ends of the trial leads are electrically coupled to color coded connectors on a trial cable (212). Trial stimulation of the trial leads is conducted to confirm lead placement (214). The stylets are removed from each of the trial leads (216) and color coded stylets are inserted in each of the trial lead lumens (218). The trial leads are then disconnected from the trial cable (220).

The epidural needles are slid off the trial lead and are removed from the patient. The incision(s) around the trial leads are closed (222). The trial leads are electrically coupled to connectors on the external pulse generator used for home trials and the exposed portions of the trial leads and the external pulse generator are attached to the patient for the home trial (224). After the home trial is completed, the trial leads are removed from the patient (226).

Figure 15A:
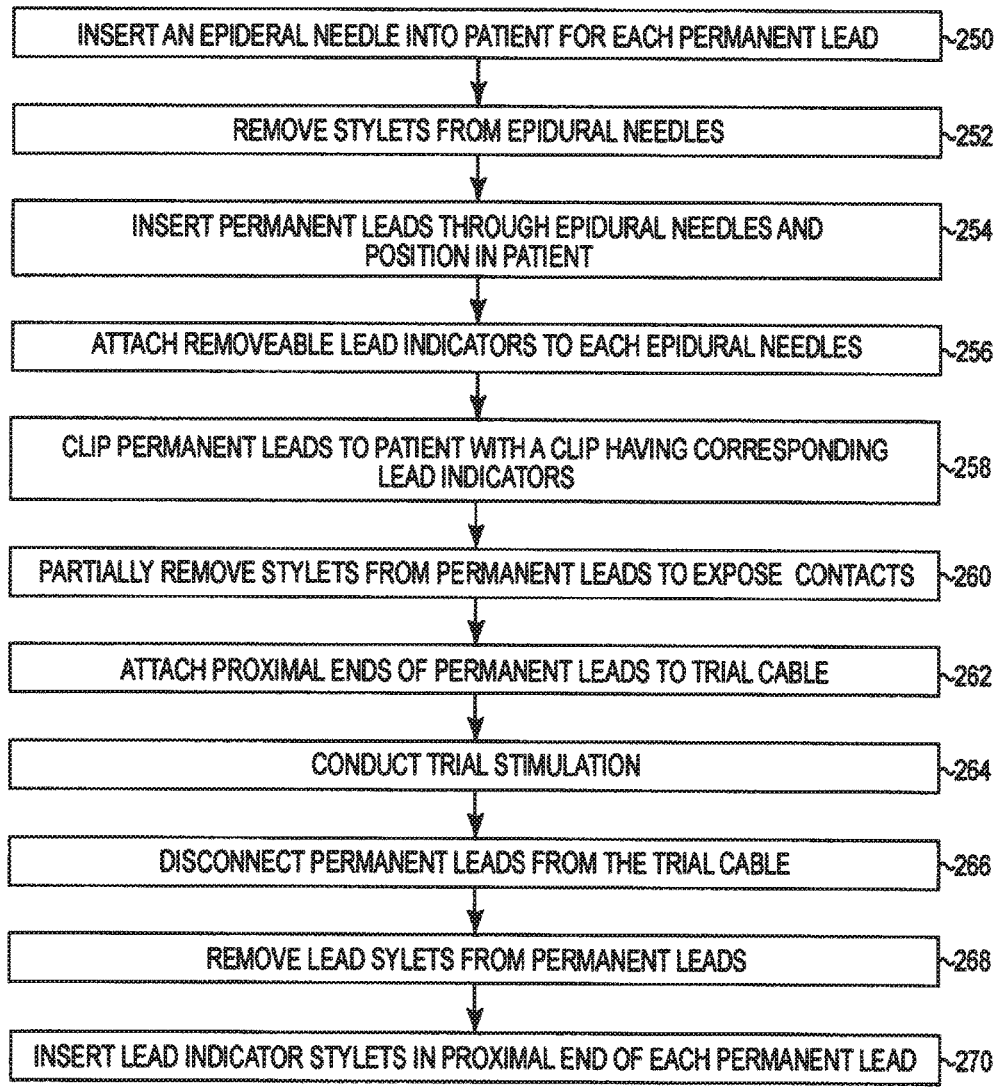
FIGS. 15A and 15B are flow charts summarizing a method for implanting a plurality of permanent leads using a lead identification system in accordance with an embodiment of the present disclosure.
Figure 15B:
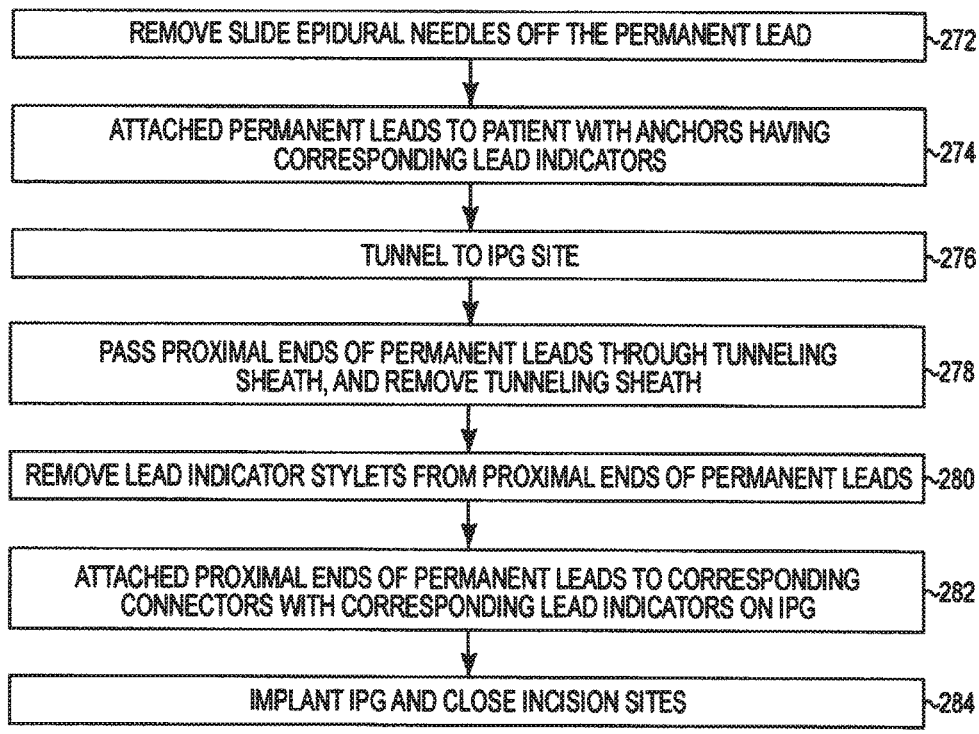

FIGS. 15A and 15B are flow charts summarizing a method for implanting a plurality of permanent leads using a lead identification system in accordance with an embodiment of the present disclosure. An epidural needle is inserted into the patient for each permanent lead (250). The stylets are removed from the epidural needles (252). The permanent leads are inserted through each epidural needle and positioned in the patient (254). A different color indicator is attached to each epidural needle (256). The permanent leads are preferably clipped to the patient using a color coded clip (258). The stylets are partially removed from each of the permanent leads to expose the contacts (260). The proximal ends of the permanent leads are electrically coupled to color coded connectors on a trial cable (262). Trial stimulation of the permanent leads is conducted to confirm lead placement (264). The permanent leads are disconnected from the trial cable (266). The stylets are removed from each of the permanent leads (268) and color coded stylets are inserted in each of the permanent lead lumens (270).

The epidural needles are slid off the permanent leads and removed from the patient (272). The permanent leads are attached to the patient using color coded anchors (274). A passageway is tunneled to the IPG site (276). Proximal ends of the permanent leads are passed through a lumen in the tunneling sheath (278). The color coded stylets are removed from the proximal ends of the permanent leads (280). The proximal ends of the permanent leads are then electrically coupled to corresponding color coded connectors on the IPG (282). The IPG is implanted and the incision sites are closed (284).

Figure 16A:
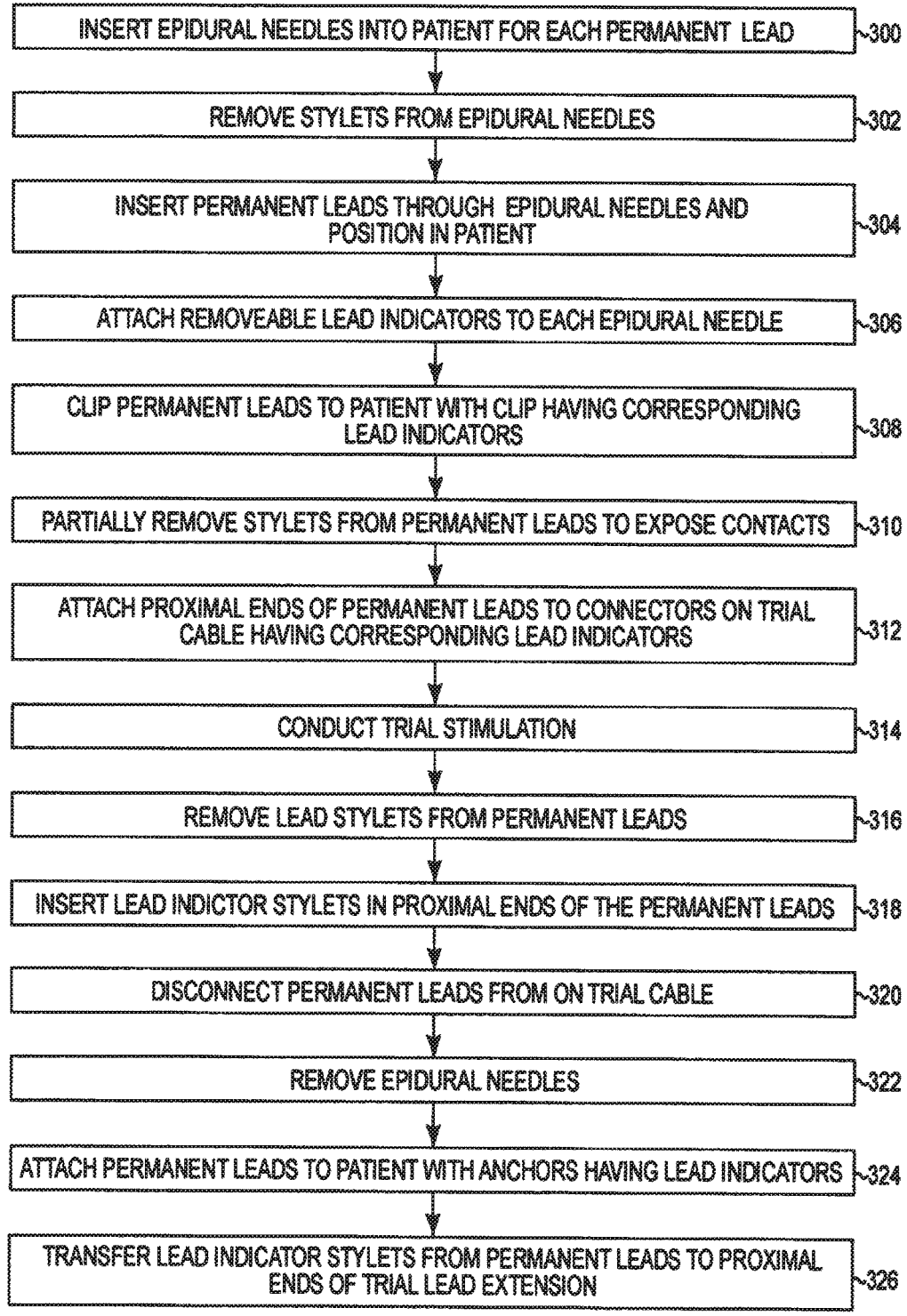
FIGS. 16A and 16B are flow charts summarizing a method for implanting a plurality of permanent leads with trial lead extensions using a lead identification system in accordance with an embodiment of the present disclosure.
Figure 16B:
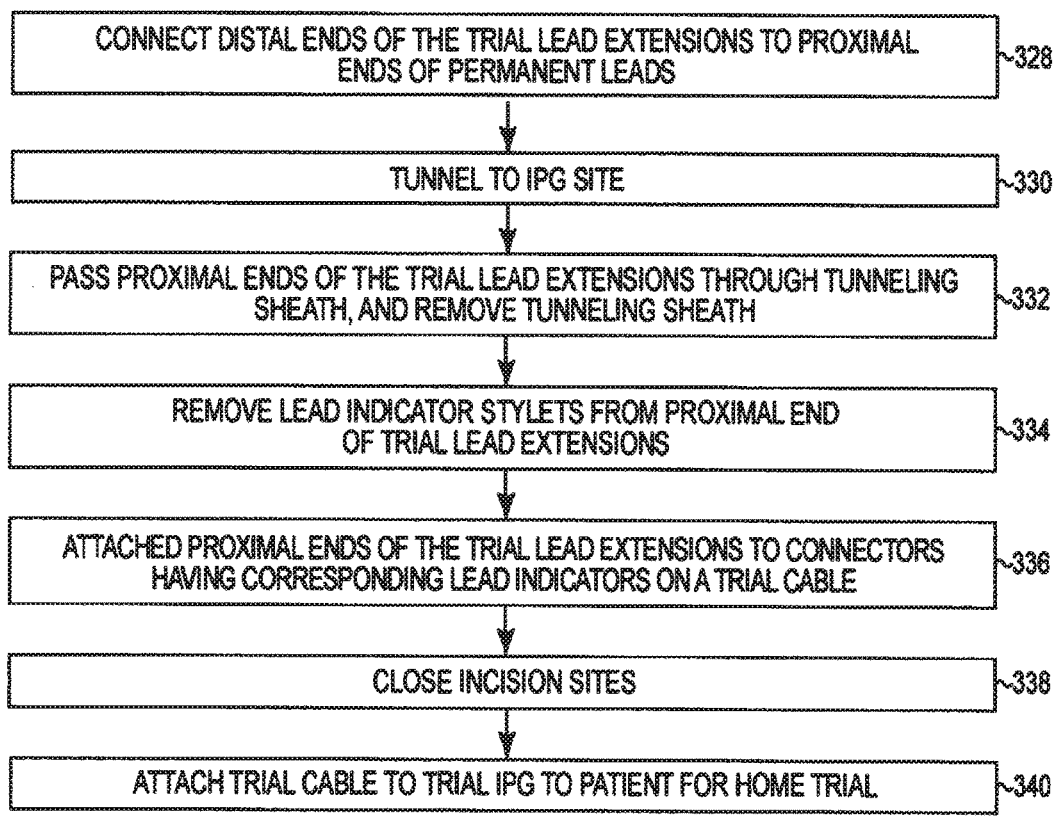

FIGS. 16A and 16B are flow charts summarizing a method for implanting a plurality of permanent leads with trial lead extensions using a lead identification system in accordance with an embodiment of the present disclosure. An epidural needle is inserted into the patient for each permanent lead (300). The stylets are removed from the epidural needles (302). The permanent leads are inserted through each epidural needle and positioned in the patient (304). A different color indicator is attached to each epidural needle (306). The permanent leads are preferably clipped to the patient using a color coded clip (308). The stylets are partially removed from each of the permanent leads to expose the contacts (310). The proximal ends of the permanent leads are electrically coupled to color coded connectors on a trial cable (312). Trial stimulation of the permanent leads is conducted to confirm lead placement (314). The stylets are removed from each of the permanent leads (316) and color coded stylets are inserted in each of the permanent lead lumens (318). The permanent leads are disconnected from the trial cable (320). The epidural needles are removed from the patient and slid off the permanent leads (322). The permanent leads are attached to the patient using color coded anchors (324). The color coded stylets are transferred from the permanent leads to proximal ends of trial lead extensions (326).

Distal ends of the trial lead extensions are connected to color coded proximal ends of the permanent leads (328). A passageway is tunneled to the IPG site (330). Proximal ends of the trial lead extensions are passed through a lumen in the tunneling sheath (332). The color coded stylets are removed from the proximal ends of the trial lead extensions (334). The proximal ends of the trial lead extensions are then electrically coupled to corresponding color coded connectors on the trial cable (336). The incision sites are closed (338). The trial pulse generator and trial cable are attached to the patient for home trial (340).

Figure 16C:
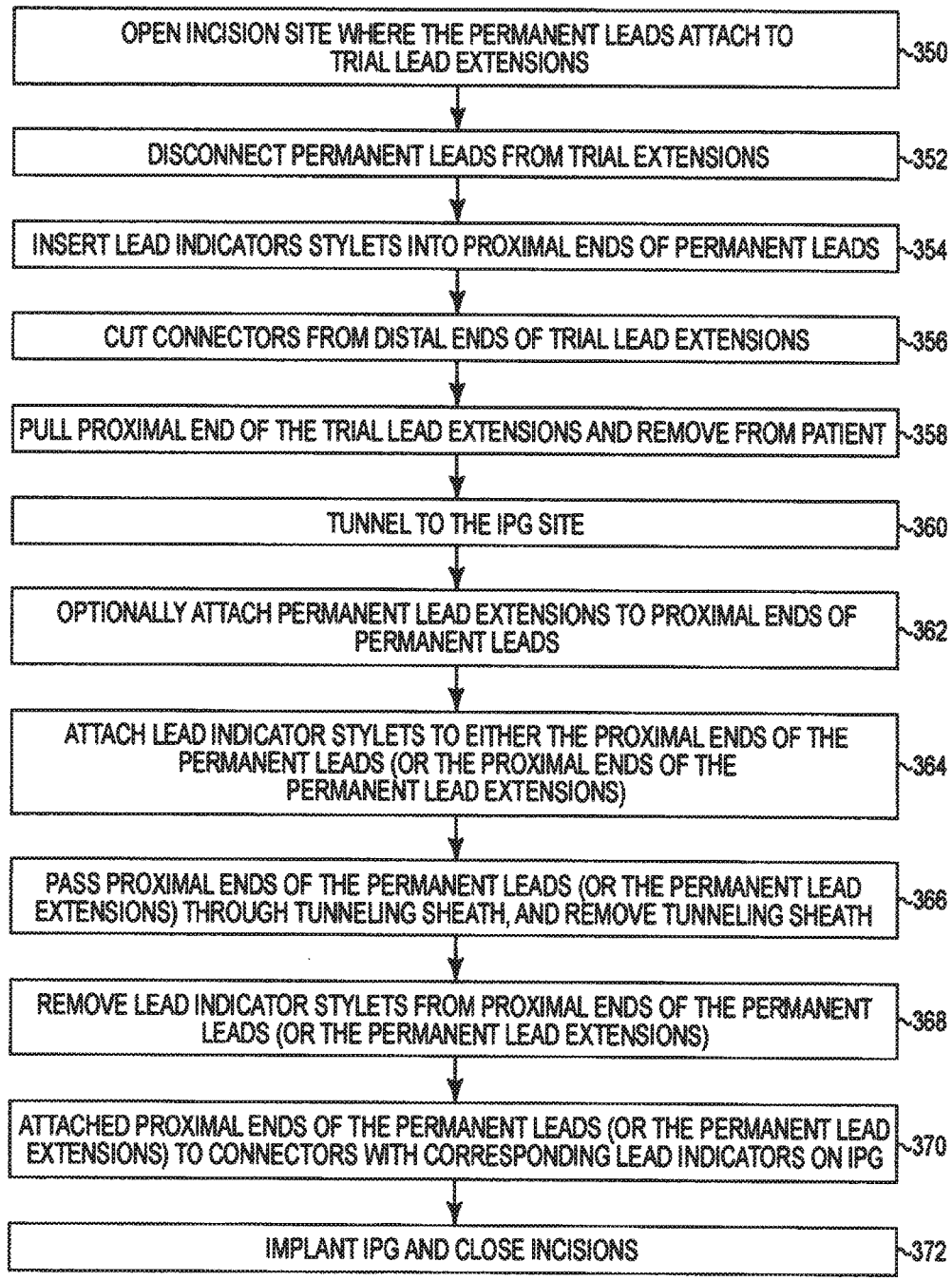
FIG. 16C is a flow chart summarizing a method of implanting a plurality of permanent leads, with or without permanent lead extensions, using a lead identification system in accordance with an embodiment of the present disclosure.

FIG. 16C is a flow chart summarizing a method for implanting a plurality of permanent leads, with or without permanent lead extensions, using a lead identification system in accordance with an embodiment of the present disclosure. The incision site where the trial lead extensions are connected to the permanent leads is opened (350). The trial lead extensions are disconnected from the permanent leads (352). Color coded stylets are inserted into proximal ends of the permanent leads (354). The connectors on the trial lead extensions are cut-off and removed from the patient (356). The proximal ends of the trial lead extensions are pulled to remove from the patient (358). A passageway is tunneled to the IPG site (360). If the permanent leads are not long enough to reach the IPG site, permanent lead extensions are attached to the permanent leads (262). Color coded stylets are inserted in the proximal ends of the permanent leads (or the proximal ends of the permanent lead extensions) (264). The proximal ends of the permanent leads (or the permanent lead extensions) are passed through the tunneling sheath, and the tunneling sheath is removed (366). The color coded stylets are removed from the proximal ends of the permanent leads (or the permanent lead extensions) (368). The proximal ends of the permanent leads (or the permanent lead extensions) are electrically coupled to corresponding color coded connectors on the IPG (370). The IPG is implanted and the incisions are closed (372).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention.

Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A method, comprising:
    inserting an epidural needle into a patient, the epidural needle having a stylet;
    removing the stylet from the epidural needle;
    inserting an implantable lead through the epidural needle, the implantable lead having a plurality of contacts;
    positioning the implantable lead; and
    attaching a removable lead indicator to the epidural needle.

2. The method of claim 1, wherein the epidural needle has an elastomeric sleeve that is rotatable.

3. The method of claim 1, further comprising:
    attaching a proximal end of the implantable lead to a trial cable;
    conducting a trial stimulation;
    thereafter disconnecting the implantable lead from the trial cable;
    removing the stylet from the implantable lead; and
    inserting a lead indicator stylet in the proximal end of the implantable lead.

4. The method of claim 3, further comprising:
    removing the epidural needle; and
    attaching the implantable lead to the patient with an anchor, the anchor having an indicator that corresponds with the removable lead indicator.

5. The method of claim 4, further comprising:
    tunneling a passageway to a site in the patient, the site being reserved for an implantable pulse generator;
    passing the proximal end of the implantable lead through a tunneling sheath; and
    removing the lead indicator stylet from the proximal end of the implantable lead.

6. The method of claim 5, further comprising:
electrically coupling the proximal end of the implantable lead to a corresponding connector on the implantable pulse generator; and
implanting the implantable pulse generator in the site.

7. The method of claim 1, wherein the implantable lead is a permanent lead.

8. The method of claim 1, wherein the implantable lead is a trial lead.

9. The method of claim 1, wherein the removable lead indicator is color-coded or has a plurality of identifying textures.

10. The method of claim 1, wherein the removable lead indicator is releasably attachable to the epidural needle.

11. The method of claim 1, wherein the removable lead indicator has an outer surface that includes a plurality of differently-sized recesses.

12. The method of claim 1, further comprising: clipping, using a clip having an indicator that corresponds with the removable lead indicator, the implantable lead to the patient.

13. The method of claim 12, wherein the clip includes a plurality of slots that are each configured to receive a proximal end of a respective implantable lead, and wherein the slots have different indicators.

14. The method of claim 1, wherein the removable lead indicator is elastically deformable.

15. A method, comprising:
inserting an epidural needle into a patient, the epidural needle having a stylet;
removing the stylet from the epidural needle;
inserting an implantable lead through the epidural needle, the implantable lead having a plurality of contacts;
positioning the implantable lead;
attaching a removable lead indicator to the epidural needle;
clipping, using a clip having an indicator that corresponds with the removable lead indicator, the implantable lead to the patient;
attaching a proximal end of the implantable lead to a trial cable;
conducting a trial stimulation;
thereafter disconnecting the implantable lead from the trial cable;
removing the stylet from the implantable lead; and
inserting a lead indicator stylet in the proximal end of the implantable lead.

16. The method of claim 15, further comprising:
removing the epidural needle;
attaching the implantable lead to the patient with an anchor, the anchor having an indicator that corresponds with the removable lead indicator;
tunneling a passageway to a site in the patient, the site being reserved for an implantable pulse generator;
passing the proximal end of the implantable lead through a tunneling sheath;
removing the lead indicator stylet from the proximal end of the implantable lead;
electrically coupling the proximal end of the implantable lead to a corresponding connector on the implantable pulse generator; and
implanting the implantable pulse generator in the site.

17. The method of claim 15, wherein the epidural needle has an elastomeric sleeve that is rotatable, and wherein the removable lead indicator is elastically deformable.

18. The method of claim 15, wherein the implantable lead is a permanent lead.

19. The method of claim 15, wherein the removable lead indicator is color-coded, or has a plurality of identifying textures, or has an outer surface that includes a plurality of differently-sized recesses.

20. A method, comprising:
inserting an epidural needle into a patient, the epidural needle having a stylet, wherein the epidural needle has an elastomeric sleeve that is rotatable;
removing the stylet from the epidural needle;
inserting an implantable lead through the epidural needle, the implantable lead having a plurality of contacts;
positioning the implantable lead;
attaching a removable lead indicator to the epidural needle, wherein the removable lead indicator is color-coded, or has a plurality of identifying textures, or has an outer surface that includes a plurality of differently-sized recesses;
clipping, using a clip having an indicator that corresponds with the removable lead indicator, the implantable lead to the patient;
attaching a proximal end of the implantable lead to a trial cable;
conducting a trial stimulation;
thereafter disconnecting the implantable lead from the trial cable;
removing the stylet from the implantable lead; and
inserting a lead indicator stylet in the proximal end of the implantable lead
removing the epidural needle;
attaching the implantable lead to the patient with an anchor, the anchor having an indicator that corresponds with the removable lead indicator;
tunneling a passageway to a site in the patient, the site being reserved for an implantable pulse generator;
passing the proximal end of the implantable lead through a tunneling sheath;
removing the lead indicator stylet from the proximal end of the implantable lead;
electrically coupling the proximal end of the implantable lead to a corresponding connector on the implantable pulse generator; and
implanting the implantable pulse generator in the site.

* * * * *